United States Patent [19]

Sun et al.

[11] Patent Number: 4,701,509
[45] Date of Patent: Oct. 20, 1987

[54] N-VINYL CAPROLACTAM-CONTAINING HOT MELT ADHESIVES

[75] Inventors: Robert L. Sun, Stanhope; James F. Kenney, Mendham, both of N.J.

[73] Assignee: Johnson & Johnson Products, Inc., New Brunswick, N.J.

[21] Appl. No.: 650,953

[22] Filed: Sep. 17, 1984

[51] Int. Cl.$^4$ .............................................. C08F 26/08
[52] U.S. Cl. ................................................... 526/264
[58] Field of Search ........................................ 526/264

[56] References Cited

U.S. PATENT DOCUMENTS

| | | | |
|---|---|---|---|
| 3,690,937 | 9/1972 | Guse et al. | 526/264 |
| 3,725,122 | 4/1973 | Reinhard et al. | 526/264 |
| 3,728,148 | 4/1973 | Peitsch et al. | 526/264 |
| 3,770,708 | 11/1973 | Knoepfel et al. | 526/264 |
| 4,164,614 | 8/1979 | Ames | 526/264 |

Primary Examiner—Joseph L. Schofer
Assistant Examiner—Peter D. Mulcahy

[57] ABSTRACT

Novel acrylate, hot melt, pressure-sensitive adhesives are disclosed which are polymerized compositions of:

| Starting Monomer | %, by Polymer Weight |
|---|---|
| 2-ethylhexyl acrylate (2-EHA) | 20–80 |
| n-butyl acrylate (BA) | 0–45 |
| isobutyl methacrylate (IBMA) | 15–25 |
| N—vinyl caprolactam (NVCL) | 10–25 | useful for medical products such as ostomy seals, adhesive tapes and bandages, wound drainage adhesive seals, wound dressings and the like that adhere well to human skin even under moist conditions.

8 Claims, No Drawings

N-VINYL CAPROLACTAM-CONTAINING HOT MELT ADHESIVES

BACKGROUND OF THE INVENTION

1. Field of the Invention

This invention relates to acrylate, hot melt, pressure-sensitive adhesives; more particularly to N-vinyl caprolactam-containing acrylate, hot melt, pressure-sensitive adhesives. More specifically, the invention relates to such adhesives which adhere well to human skin and are useful for medical products and which adhesives are polymerized compositions containing 2-ethylhexyl acrylate (2-EHA), isobutyl methacrylate (IBMA), N-vinyl caprolactam (NVCL) and optionally, but preferably, n-butyl acrylate (BA) as well, many of which adhesives adhere well to skin even under moist conditions.

The hot melt adhesive possesses the reversible properties of strong cohesive strength at ambient temperature and desirable melt viscosity at elevated coating temperatures. The present invention provides a process for making the hot melt adhesive as well as a process for making ostomy seals, adhesive tapes and bandages, wound drainage adhesive seals, wound dressings and the like that adhere to human skin and remain adherent even in a moist environment.

2. Prior Art

Although many adhesive compositions are known, very few of these are completely satisfactory for application to human skin. The requirements for such adhesives are stringent; they must adhere well to human skin during perspiration, when the weather is hot, or in an environment of draining wounds, yet be removable without leaving adhesive residue on the skin's surface. Numerous homopolymers, copolymers and terpolymers have been proposed for use as polymeric adhesives. The demands of modern technology, however, are for even higher requirements of adhesion and cohesion. Adhesion should take effect immediately on application to skin, even in a hot or moist environment, and should release cleanly when voluntarily removed in this environment.

Many acrylate homopolymers, copolymers and terpolymers previously used as medical adhesives lose adhesion in a moist environment. In the prior art, acrylic esters have been copolymerized with small portions of monomers such as acrylic acid, methacrylic acid, itaconic acid, acrylamide, methacrylamide, acrylic esters, vinyl esters, n-alkoxy-alkyl unsaturated carboxylic acid amides, half esters, half amides, amide esters, amides and imides of maleic anhydride, and the alkylaminoalkylene monoesters of maleic, itaconic or citraconic acids. Although the use of these compositions results in adhesives which adhere well to dry skin, many of these compositions lose adhesiveness in a hot or moist environment. U.S. Pat. No. 4,379,881 discloses an acrylic adhesive containing acrylic acid that adheres to skin under dry and moist conditions.

Not withstanding the utility and commercial success of acrylic pressure-sensitive adhesives, there are numerous applications of medical adhesives requiring such outstanding adhesive performance, in a moist environment, that presently available pressure-sensitive adhesives have not been entirely satisfactory. Thus, there is a need for pressure-sensitive adhesives having improved adhesion to skin for ostomy adhesive seals, wound drainage adhesive seals, surgical tapes, dressings, drapes, adhesive bandages, and the like.

In the past, attempts have been made to produce acrylicbased hot melt adhesives by incorporating 0.5 to 25% by weight of metallic chelating agents, such as zinc or cadmium salts to an amine-containing copolymer. The produced adhesives possess non-permanent, reversible bonds and showed an increase in Williams Plasticity Number from 0.93 to 1.25 mm (U.S. Pat. No. 3,925,282).

Another method found in the patent literature for improving cohesive strength of acrylic-based, hot melt adhesives is blending two copolymers, one copolymer containing a tertiary amine group, and the other has a built-in organic acid group. Upon mixing, a reversible ionic bonding is formed. (U.S. Pat. No. 4,405,517).

U.S. Pat. No. 4,337,325 (Shah), The Kendall Company, discloses hot melt, pressure-sensitive compositions comprising a blend of copolymers consisting of acrylic monomers and vinyl lactam, and can use N-vinyl caprolactam. The copolymer adhesive blend exhibits a viscosity less than 100,000 cps at 350° F. (Applicant does not use blends, but rather uses only a single polymer component consisting of 3 or 4 monomers to make the adhesive of the present invention.)

U.S. Pat. No. 4,379,881 (R. F. Peck), Smith and Nephew Company, discloses an adhesive polyacrylate containing n-butyl acrylate, 2-ethylhexyl acrylate and acrylic acid that may be used for dressings and adheres firmly to skin under dry and moist conditions.

U.S. Pat. No. 4,164,614 (Ames), Eastman Kodak, discloses hot melt adhesive compositions containing 2-ethylhexyl acrylate, N-vinyl-2-pyrrolidone and styrene.

In addition, additional hot melt, pressure-sensitive adhesive compositions are disclosed in U.S. Pat. No. 4,423,182.

The prior art hot melt adhesives all differ significantly from those of the present invention in various respects particularly in lacking N-vinyl caprolactam (NVCL) which is a key component of the polymerized composition of the present invention. An improved hot melt, pressure-sensitive adhesive requires higher Williams Plasticity Numbers to avoid cold flow, above 1.5 mm. An adhesive for medical usage generally has higher requirements, such as no skin irritation, clarity, colorlessness, and higher moduli for lower adhesive transfer to skin. Hot melt adhesives from amine-containing monomers have a high tendency of discoloring and metallic chelating agents may cause skin irritation. Currently available hot melt pressure-sensitive adhesive exhibit acceptable tack, however, the cold flow, creep resistance and low modulus properties need improvement.

The novel hot melt, pressure-sensitive adhesives of the present invention utilize acrylic monomers which contain neither organic amine, nor acid functional groups, nor metallic salts. The hot melt adhesives of the present invention are polymerized compositions containing 2-ethylhexyl acrylate, isobutyl methacrylate, and N-vinyl caprolactam and may also contain, as an optional ingredient for the preferred adhesive, n-butyl acrylate.

It should be understood that while their medical uses will be emphasized herein, the adhesives of the present invention can also be used for various non-medical adhesive applications which may have much less stringent requirements in regard to various properties, and the less preferred adhesives of the present invention could be so used.

It is accordingly an object of the present invention to provide an improved medical pressure-sensitive adhesive. It is a further object of the present invention to provide a hot melt, pressure-sensitive adhesive having improved wear performance, particularly having good adhesion to skin under hot or moist conditions where skin perspiration or draining wound affects adhesion. The present invention further provides an economical process for making the adhesive composition and a method for coating the adhesive onto a substrate.

SUMMARY OF THE INVENTION

A novel medical, acrylic, hot melt, pressure-sensitive adhesive is disclosed that possesses high adhesive strength to human skin and high cohesive strength that remains adhered to skin, and on voluntary removal negligible adhesive transfer to skin occurs. The adhesive is a polymerized composition containing:

2-ethylhexyl acrylate (2-EHA),
isobutyl methacrylate (IBMA),
N-vinyl caprolactam (NVCL), and optionally, n-butyl acrylate (BA), which monomers may be used in a range, expressed as percent by polymer weight, of:

|       | BROAD RANGE % | PREFERRED RANGE % | MOST PREFERRED RANGE % |
|-------|---------------|-------------------|------------------------|
| 2-EHA | 20-80         | 30-65             | 35-50                  |
| BA    | 0-45          | 0-35              | 15-35                  |
| IBMA  | 15-25         | 15-25             | 15-25                  |
| NVCL  | 10-25         | 15-20             | 15-20                  | which broad range compositions adhere well to dry skin and which preferred range compositions adhere to human skin even in a moist environment, i.e., exhibit wet-stick. The most preferred compositions, for medical purposes, are made with all four monomers.

The adhesive of the present invention has a Williams Plasticity Number sufficiently high to be useful, generally above 1.5 millimeters (mm), preferably 1.5 to 2.5 mm, and a melt viscosity permitting its application with modern equipment, e.g., from 40,000 to 350,000 centipoises (cps) at 350° F.

The adhesive compositions, of the present invention can be prepared by a process of solution polymerization. Catalysts generally used in solution polymerizations such as azo compounds, peroxy ester or peroxides are suitable for polymerization. The preferred catalyst is azobisisobutyronitrile. The amount of catalyst used is preferably between 0.05 percent to 1 percent based on the total monomer weight. The polymerization may contain a mercaptan compound to regulate or control the polymer molecular weight and adhesive melt viscosity. Tert-dodecyl mercaptan, n-dodecyl mercaptan, and trimethylol propane trimercaptopropionate are suitable for the polymerization. The amount of mercaptan used is perferably between zero to 0.5 percent.

For medical, pressure-sensitive adhesive sheet products, the hot melt adhesive is coated onto an appropriate backing substrate which may be a porous or nonporous material. Representative porous materials include polyurethane films, paper, and woven and nonwoven fabrics which may be composed of wood pulp, rayon, polyester, acetate fibers, cotton fibers, and blend combinations such as wood pulp and rayon, and wood pulp and polyester. Nonporous backings can be films of polyvinyl chloride, polyethylene, polypropylene and the like.

The preferred novel hot melt adhesive compositions can produce medical adhesive sheet products which are substantially free from the disadvantages of most medical adhesive products known in the art. The adhesive polymer according to the present invention is distinguished in particular by the following advantages: medical adhesive products prepared with the hot melt adhesive exhibit firm adhesion to moist skin; such medical adhesive products exhibit excellent long-term adhesion to skin; the hot melt adhesive exhibits excellent resistance to degradation by water, sweat, urine, high pH and low pH; and the hot melt adhesive has optimum melt viscosity for coating on substrates and excellent resistance to cold flow resulting in only trace amount of adhesive transfer to skin.

For medical applications adhesives are often sterilized. The adhesives of the present invention may be sterilized, e.g., using cobalt 60 irradiation (and very likely by the use of ethylene oxide) which does not significantly effect their properties and characteristics, but need not be sterilized where sterilization is not needed for the use desired.

The hot melt adhesive of the present invention is evaluated by coating the adhesive on a backing material on a reverse-roll or slot die hot melt coating machine, or the adhesive may be coated on release paper for transfer to the backing. Prototypes of medical products which ideally are required to adhere to human skin and remain adherent even in a moist environment, such as ostomy adhesive seals, wound drainage adhesive seals, ulcer dressings, adhesive tapes, and adhesive bandages are made and wear performance tested on human subjects or animals. The medical product prototypes made with the hot melt adhesive of the present invention are compared in wear performance with commercial adhesive medical products.

The invention will be described in greater detail by the following examples, in which all parts are by weight. As a quantitative aid to evaluating products of the present invention, it has been found helpful to employ certain empirical tests, which tests will now be described in more detail.

Williams Plasticity Number—This property which indicates the deformability of the adhesive mass under static load is measured using a Williams Plastometer, manufactured by Scott Testers, Inc., following the procedures of ASTM Method D-926.

Melt Viscosity—This property which indicates the viscosity of the hot, fluid adhesive at the coating temperature is measured using a Brookfield Thermosel Viscometer and a Number 28 spindle.

Wear Performance Test—Twenty-four human subjects are utilized for each test. Six to eight 1×3 inch strips of adhesive tape are applied to the upper arm, back or fingers, and subjects are allowed to engage in normal activities and bathing habits. At the end of 24 hours, or 72 hours, adhesion readings are taken. Skin redness, degree of skin strippage and adhesive left on the skin are noted and recorded. Adhesion is rated from 0 (tape off) to 7 (perfect adhesion). Adhesive transfer is rated from 0 (no residue) to 10 (heavy residue).

Wet-stick Adhesion Test—A sample adhesive, 2-60 mils in thickness, 1×3 inches was placed on clean wet skin on the back of the hand. The adhesive was allowed to stay in place for 5 minutes and then removed from the skin. The degree of adhesion was observed as well as the resistance to removal. The degree of adhesion was noted as good or poor.

Actual test results obtained are found in Tables I–V, and are reported as the average for all test subjects.

Any adhesive composition of the present invention having good wet-stick performance will always have good dry-stick performance as well. Some three component compositions, i.e., without the optional n-butyl acrylate (BA) component, seem to exhibit good wet-stick performance while others exhibit only dry-stick adhesive performance. The wet-stick adhesion performance is somewhat dependent on the level of NVCL in the composition. With less than about 15% NVCL, wet-stick adhesion to wet skin is poor, while with above about 25% NVCL, the composition is too stiff or too hard and lacks adhesive character.

The examples set forth below will serve to illustrate the invention in certain of its embodiments without acting as a limitation upon its scope.

Examples 1–4 and 7–10 illustrate various four-component adhesives, all within the scope of the present invention, containing 2-EHA, BA, IBMA and NVCL. Example 5 illustrates a two component adhesive containing 2-EHA and NVCL which is outside the scope of the present invention. Example 6 illustrates a three component adhesive without any BA, which is a less preferred form of the present invention being effective on dry skin but not on moist skin.

Examples 1–7 and 9–10 illustrate various representative batch polymerizations while Example 8 illustrates a different type of process involving a slow feed over a period of several hours. Differing conditions and ingredients are shown to result in adhesives with different physical characteristics.

The various Examples also serve to illustrate how persons skilled in the art can make various well-known medical devices utilizing the adhesives of the present invention.

EXAMPLE 1

A 5-liter, 4-neck, round-bottom flask was fitted with a Teflon blade stirrer, a water condenser, a thermometer, and a nitrogen inlet tube. The following ingredients were added to the flask:

| | |
|---|---|
| Toluene (dried) | 1350 g |
| 2-ethylhexyl acrylate | 675 g |
| n-butyl acrylate | 300 g |
| isobutyl methacrylate | 300 g |
| N—vinyl caprolactam | 225 g |

When all the ingredients were in the flask, a slow nitrogen flow was started under the surface of the liquid. Nitrogen flow was continued throughout the polymerization. The flask was immersed in a water bath, rapid stirring was started, and heated to 60° C. Azobisisobutyronitrile (sold by DuPont as Vazo 64) 3.75 g in 90 g toluene were added to the flask. The temperature was maintained at 60° C. and polymerization continued for five hours. At the end of five hours, 0.60 g azobisisobutyronitrile in 60 g of toluene was added to the flask and the temperature of the flask raised to 70° C. and maintained for one hour. The polymer solution was cooled and discharged from the flask.

Toluene was evaporated from the adhesive polymer in a vacuum oven at 70° C. The melt viscosities of the adhesive were determined with a Brookfield Thermosel Viscometer using Number 28 spindle and were 350,000, 150,000 and 40,000 cps at 300, 350 and 400° F., respectively. The Williams Plasticity Number of the adhesive was 1.8 mm. The adhesive exhibited firm adhesion to the moist skin on the back of the hand.

The hot melt adhesive was coated on a slot die laboratory model hot melt coating machine at 375° F. at a speed of 6 feet per minute onto silicone release paper and transferred to an ethylene-acrylic acid copolymer film backing material. Adhesive tape strips were made and exposed to 2.5 Mrad of $Co^{60}$ radiation. The wear performance of the tape was excellent with a high adhesion to skin and low adhesive transfer as shown in Table I.

The hot melt adhesive was coated on a flexible polyvinyl chloride film at 1.6 oz/yd$^2$ coating weight using a laboratory model slot die hot melt coating machine. The thickness of the adhesive was 2 mils.

Adhesive bandage strips were made. A portion of the strips was exposed to 2.5Mrad of $Co^{60}$ radiation. The wear performance of the unexposed and exposed adhesive bandage strips was excellent with high adhesion to skin and low adhesive transfer as shown in Tables II and III.

EXAMPLE 2

The polymerization of Example 1 was repeated. The Williams Plasticity Number of the adhesive was 1.7 mm and the melt viscosity at 350° F. was 158,000 cps. The adhesive exhibited firm adhesion to the moist skin on the back of the hand. The polymer adhesive solution was cast onto an ethylene-acrylic acid copolymer film. The solvent was evaporated resulting in an adhesive of 25 mils thickness.

The adhesive film was exposed to 2.5 Mrad of $Co^{60}$ radiation. The wear performance was excellent with high adhesion to skin and low adhesive transfer as shown in Table I.

EXAMPLE 3

The polymerization procedure of Example 1 was repeated, except 0.45 g tert-dodecyl mercaptan was added to the monomer mixture. The Williams Plasticity Number of the adhesive was 1.9 mm and the melt viscosity at 350° F. was 156,000 cps. The adhesive exhibited firm adhesion to the moist skin on the back of the hand. The polymer adhesive solution was cast onto an ethylene-acrylic acid copolymer film. The solvent was evaporated resulting in an adhesive of 60 mils thickness. The adhesive was exposed to $Co^{60}$ radiation at 2.5 Mrad. The wear performance was acceptable with good adhesion to skin and low adhesive transfer as shown in Table I.

The hot melt adhesive was coated on a flexible polyvinyl chloride film backing at 1.6 oz/yd$^2$ coating weight using a laboratory model slot die hot melt coating machine. Adhesive bandage strips were made and exposed to 2.5 Mrad of $Co^{60}$ radiation. The wear performance of the adhesive bandage strips was excellent with high adhesion to skin and low adhesive transfer as shown in Tables IV and V.

EXAMPLE 4

The polymerization procedure of Example 1 was repeated. The solid adhesive polymer had a melt viscosity of 232,000 cps at 350° F. The adhesive was exposed to $Co^{60}$ radiation at 2.5 Mrad, afterwards the Williams Plasticity Number was 2.0 mm. The adhesive exhibited firm adhesion to moist skin on the back of the hand. The solid polymer adhesive was coated via a hot melt coating machine onto a polyvinyl chloride film backing. The thickness of the adhesive coating was 8 mils. Adhesive strips were made and exposed to 2.5 Mrad of $Co^{60}$ radiation. The wear performance was excellent with high adhesion to skin and acceptable adhesive transfer as shown in Tables I, IV and V.

EXAMPLE 5

The polymerization procedure of Example 1 was repeated, except a monomer composition of 80 percent 2-EHA and 20 percent NVCL was polymerized. The solid adhesive polymer had a melt viscosity of 44,000 cps at 350° F. and a Williams Plasticity Number of 1.1 mm. The plasticity number was too low to be acceptable as an adhesive for application to skin.

EXAMPLE 6

The polymerization procedure of Example 1 was repeated, except a monomer composition of 55 percent 2-EHA, 25 percent IBMA and 20 percent NVCL was polymerized. The solid adhesive polymer had a melt viscosity of 100,000 cps at 350° F. and a Williams Plasticity Number of 2.1 mm. The adhesive exhibited a low level of adhesion to the moist skin (but a good level of adhesion to the dry skin) on the back of the hand. The adhesion of this Example is considered acceptable although the adhesive was not coated on a substrate and wear performance evaluated.

EXAMPLE 7

The polymerization procedure of Example 1 was repeated, except a monomer composition of 30 percent 2-EHA, 35 percent BA, 20 percent IBMA and 15 percent NVCL was polymerized. The solid adhesive polymer had a melt viscosity of 360,000 cps at 350° F. and a Williams Plasticity Number of 1.9 mm. The adhesion of this Example is considered acceptable although the adhesive was not coated on a substrate and wear performance evaluated.

EXAMPLE 8

A 2-liter, 4-neck, round-bottom flask was fitted with a Teflon blade stirrer, a water condenser, a thermometer, and a nitrogen inlet tube. A monomer composition of 45 percent 2-EHA, 15 percent BA, 20 percent IBMA, and 20 percent NVC was polymerized according to the following procedure.

The flask was purged with nitrogen. To the flask, with rapid stirring, were added 450 g toluene and 75 g of the monomer mixture. The flask was heated to 60° C. and 5 g of a catalyst solution (1.2 g azobisisobutyronitrile dissolved in 30 g toluene) were added. Polymerization was continued for one-half hour. Then, 425 g of monomer mixture and 26.2 g catalyst solution were added over four hours to the flask at 60° C. The polymerization was allowed to continue for an additional one-half hour at 60° C. To the flask, at 60° C., was added 0.2 g azobisisobutyronitrile dissolved in 20g toluene. Polymerization was continued for an additional one hour. The solid adhesive polymer had a melt viscosity of 76,000 cps at 350° F. and a Williams Plasticity Number of 1.7 mm. The adhesion of this Example is considered acceptable although the adhesive was not coated on a substrate and wear performance evaluated.

EXAMPLE 9

The polymerization procedure of Example 1 was repeated. The solid adhesive polymer had a melt viscosity of 270,000 cps at 350° F. and a Williams Plasticity Number of 1.7 mm. After exposure to 2.5 Mrad $Co^{60}$ radiation, the Williams Plasticity Number was 2.0 mm. The adhesive exhibited firm adhesion to the moist skin of the back of the hand.

The hot melt adhesive was coated on a flexible polyvinyl chloride film at 1.6 oz/yd$^2$ coating weight using a laboratory model slot die hot melt coating machine. Adhesive bandage strips were made and exposed to 2.5 Mrad of $Co^{60}$ radiation. The wear performance of the adhesive bandage strips was excellent with high adhesion to skin and low adhesion transfer as shown in Tables II and III.

EXAMPLE 10

The polymerization procedure of Example 1 was repeated. The solid adhesive polymer had a melt viscosity of 100,000 cps at 350° F. and a Williams Plasticity Number of 2.2 mm. After exposure to 2.5 Mrad of $Co^{60}$ radiation, the williams Plasticity Number was 2.5 mm. The adhesive exhibited firm adhesion to the moist skin of the back of the hand.

A 50-mil thick sheet of adhesive was applied to a one-mil thick polyurethane film and evaluated as a dressing for a full-thickness incision made on a guinea pig. The adhesive side was placed directly in contact with and over the incision and remained for eight days. The incision healed rapidly, without irritation, and with remarkably little scarring.

Test Results

Various adhesives of the preceding Examples were tested by the methods previously described and the results are depicted in the following Tables I–V. In said tests, one of two controls was used, i.e., "Stomahesive" or Plastic Adhesive Bandage.

"Stomahesive" is a commercial product of the Convatec Division of Squibb, and is a physical blend of polyisobutylene, gelatin, pectin and sodium carboxymethyl cellulose. Stomahesive adheres to dry skin and moist skin; it is sold as an adhesive product for use to attach ostomy appliances (bags or pouches) to the skin around a stoma, in sheets 4"×4" or 8"×8" long and 60 mils thick.

Plastic Adhesive Bandage is a commercial product of Johnson & Johnson Products, Inc. It is a formulated adhesive based on natural rubber and a tackifier. The thickness of the adhesive is 2 mils.

In the following tables, "Unexposed" refers to nonexposure to radiation sterilization. All other samples were exposed to radiation sterilization.

TABLE I

| | WEAR PERFORMANCE OF ADHESIVE APPLIED TO BACK | | | |
|---|---|---|---|---|
| Example | Adhesive Composition | Average Adhesion 24 hr | 72 hr | Average Adhesive Transfer 72 hr |
| 1 | 2-EHA/BA/IBMA/NVCL 45/20/20/15 | 6.6 | 6.7 | 0.8 |
| 2 | 2-EHA/BA/IBMA/NVCL 45/20/20/15 | 6.1 | 5.8 | 0.7 |
| 3 | 2-EHA/BA/IBMA/NVCL 45/20/20/15 | 5.5 | 4.8 | 0.7 |

TABLE I-continued
WEAR PERFORMANCE OF ADHESIVE APPLIED TO BACK

| Example | Adhesive Composition | Average Adhesion 24 hr | Average Adhesion 72 hr | Average Adhesive Transfer 72 hr |
|---|---|---|---|---|
| 4 | 2-EHA/BA/IBMA/NVCL 45/20/20/15 | 6.7 | 6.2 | 0.9 |
| Control | Stomahesive | 6.6 | 6.0 | 0.8 |

TABLE II
WEAR PERFORMANCE OF ADHESIVE APPLIED TO UPPER ARM

| Example | Adhesive Composition | Average Adhesion | Average Adhesive Transfer |
|---|---|---|---|
| 1 (Unexposed) | 2-EHA/BA/IBMA/NVCL 45/20/20/15 | 6.8 | 0.9 |
| 1 | 2-EHA/BA/IBMA/NVCL 45/20/20/15 | 6.8 | 0.6 |
| 9 | 2-EHA/BA/IBMA/NVCL 45/20/20/15 | 6.7 | 0.6 |
| Control | Plastic Adhesive Bandage | 6.4 | 0.6 |

TABLE III
WEAR PERFORMANCE OF ADHESIVE APPLIED TO FINGER

| Example | Adhesive Composition | Average Adhesion | Average Adhesive Transfer |
|---|---|---|---|
| 1 (Unexposed) | 2-EHA/BA/IBMA/NVCL 45/20/20/15 | 6.4 | 1.0 |
| 1 | 2-EHA/BA/IBMA/NVCL 45/20/20/15 | 6.4 | 0.7 |
| 9 | 2-EHA/BA/IBMA/NVCL 45/20/20/15 | 6.4 | 0.8 |
| Control | Plastic Adhesive Bandage | 6.4 | 0.6 |

TABLE IV
WEAR PERFORMANCE OF ADHESIVE APPLIED TO UPPER ARM

| Example | Adhesive Composition | Average Adhesion | Average Adhesive Transfer |
|---|---|---|---|
| 3 | 2-EHA/BA/IBMA/NVCL 45/20/20/15 | 6.9 | 0.9 |
| 4 | 2-EHA/BA/IBMA/NVCL 45/20/20/15 | 6.8 | 0.7 |
| Control | Plastic Adhesive Bandage | 6.8 | 0.7 |

TABLE V
WEAR PERFORMANCE OF ADHESIVE APPLIED TO FINGER

| Example | Adhesive Composition | Average Adhesion | Average Adhesive Transfer |
|---|---|---|---|
| 3 | 2-EHA/BA/IBMA/NVCL 45/20/20/15 | 6.1 | 0.9 |
| 4 | 2-EHA/BA/IBMA/NVCL 45/20/20/15 | 6.4 | 0.7 |
| Control | Plastic Adhesive Bandage | 6.4 | 0.7 |

What is claimed is:

1. A hot melt pressure-sensitive adhesive, suitable for medical use, consisting of a polymerized composition of 20 to 80 percent 2-ethylhexyl acrylate, 0 to 45 percent n-butyl acrylate, 15 to 25 percent isobutyl methacrylate and 10 to 25 percent N-vinyl caprolactam.

2. A hot melt adhesive according to claim 11 wherein the polymerized composition consists of 30 to 65 percent 2-ethylhexyl acrylate, 0 to 35 percent n-butyl acrylate, 15 to 25 percent isobutyl methacrylate and 15 to 20 percent N-vinyl caprolactam.

3. A hot melt adhesive according to claim 12, having a Williams Plasticity Number above 1.5 mm.

4. A hot melt adhesive according to claim 12, having a melt viscosity at 350° F. from 40,000 to 350,000 cps.

5. A hot melt adhesive according to claim 3, which has been sterilized.

6. A hot melt adhesive according to claim 3 wherein the polymerized composition consists of 35 to 50 percent 2-ethylhexyl acrylate, 15 to 35 percent n-butyl acrylate, 15 to 25 percent isobutyl methacrylate, and 15 to 20 percent N-vinyl caprolactam.

7. A hot melt adhesive according to claim 6 wherein the polymerized composition consists of 45 percent 2-ethylhexyl acrylate, 20 percent n-butyl acrylate, 20 percent isobutyl methacrylate, and 15 percent N-vinyl caprolactam.

8. A hot melt adhesive according to claim 7, having a Williams Plasticity Number of 1.5 to 2.5 mm.

* * * * *

UNITED STATES PATENT AND TRADEMARK OFFICE
CERTIFICATE OF CORRECTION

PATENT NO. : 4,701,509
DATED : October 20, 1987
INVENTOR(S) : Sun et al.

It is certified that error appears in the above-identified patent and that said Letters Patent is hereby corrected as shown below:

Column 10, Claim 2, line 31, "11" should be -- 1 --;

Column 10, Claim 3, line 36, "12" should be -- 2 --; and

Column 10, Claim 4, line 38, "12" should be -- 2 --.

Signed and Sealed this

Twenty-first Day of June, 1988

Attest:

DONALD J. QUIGG

Attesting Officer

Commissioner of Patents and Trademarks